United States Patent
Guan et al.

(10) Patent No.: US 11,654,203 B2
(45) Date of Patent: May 23, 2023

(54) DUAL-TARGETED CARBONIC ANHYDRASE IX COMPLEX AND CONTRAST AGENT THEREOF

(71) Applicant: Institute of Nuclear Energy Research, Atomic Energy Council, Executive Yuan, R.O.C, Taoyuan (TW)

(72) Inventors: Siao-Syun Guan, Taoyuan (TW);
Tsai-Yueh Luo, Taoyuan (TW);
Tse-Zung Liao, Taoyuan (TW);
Cheng-Liang Peng, Taoyuan (TW);
Kun-Liang Lin, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 165 days.

(21) Appl. No.: 17/079,691

(22) Filed: Oct. 26, 2020

(65) Prior Publication Data
US 2021/0154334 A1    May 27, 2021

(30) Foreign Application Priority Data
Nov. 22, 2019   (TW) ................. 108142431

(51) Int. Cl.
| A61K 49/14 | (2006.01) |
| A61K 49/10 | (2006.01) |
| A61K 47/54 | (2017.01) |
| C12N 9/88 | (2006.01) |

(52) U.S. Cl.
CPC ............. *A61K 49/14* (2013.01); *A61K 47/54* (2017.08); *A61K 49/106* (2013.01); *C12N 9/88* (2013.01); *C12Y 402/01001* (2013.01)

(58) Field of Classification Search
CPC ...... A61K 49/00; A61K 49/14; A61K 49/106; A61K 47/00; A61K 47/54; A61K 51/00; A61K 51/08; A61K 51/088; C12N 9/88; C12Y 402/01001
USPC ............... 424/1.11, 1.65, 1.69, 9.1; 530/300; 514/1, 1.1; 534/7, 10–16
See application file for complete search history.

(56) References Cited

PUBLICATIONS

Guan et al, Oncotarget, vol. 6, No. 34, pp. 36139-36155 (Year: 2015).*
Rana et al, Plos One, vol. 7, Issue 5, e38279 (Year: 2012).*

* cited by examiner

*Primary Examiner* — D. L. Jones
(74) *Attorney, Agent, or Firm* — Locke Lord LLP; Tim Tingkang Xia, Esq.

(57) ABSTRACT

Disclosed herein are a dual-targeted carbonic anhydrase IX complex, a contrast agent comprising the same, and a synthesizing method thereof. The dual-targeted carbonic anhydrase IX complex includes a carbonic anhydrase IX (CA9) binding peptide, a sulfonamide derivative, and a metal chelating agent. The dual-targeted carbonic anhydrase IX complex has potential for use as a molecular nuclear drug.

7 Claims, 3 Drawing Sheets
Specification includes a Sequence Listing.

SEQUENCE LISTING

<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: synthesized

<400> SEQUENCE: 1

Asn His Val Pro Leu Ser Pro
1               5

<210> SEQ ID NO 2
<211> LENGTH: 7
<212> TYPE: PRT
<213> ORGANISM: Artificial Sequence
<220> FEATURE:
<223> OTHER INFORMATION: synthesized

<400> SEQUENCE: 2

Gly Gly Gly Cys Gly Gly Gly
1               5

<210> SEQ ID NO 3
<211> LENGTH: 9
<212> TYPE: PRT
<213> ORGANISM: Artificial Sequence
<220> FEATURE:
<223> OTHER INFORMATION: synthesized

<400> SEQUENCE: 3

Gly Gly Gly Gly Cys Gly Gly Gly Gly
1               5

<210> SEQ ID NO 4
<211> LENGTH: 11
<212> TYPE: PRT
<213> ORGANISM: Artificial Sequence
<220> FEATURE:
<223> OTHER INFORMATION: synthesized

<400> SEQUENCE: 4

Gly Gly Gly Gly Gly Cys Gly Gly Gly Gly Gly
1               5                   10

<210> SEQ ID NO 5
<211> LENGTH: 13
<212> TYPE: PRT
<213> ORGANISM: Artificial Sequence
<220> FEATURE:
<223> OTHER INFORMATION: synthesized

<400> SEQUENCE: 5

Gly Gly Gly Gly Gly Gly Cys Gly Gly Gly Gly Gly Gly
1               5                   10

<210> SEQ ID NO 6
<211> LENGTH: 14
<212> TYPE: PRT

```
<213> ORGANISM: Artificial Sequence
<220> FEATURE:
<223> OTHER INFORMATION: CA9tp;synthesized

<400> SEQUENCE: 6

Asn His Val Pro Leu Ser Pro Gly Gly Gly Cys Gly Gly Gly
1               5                   10
```

DUAL-TARGETED CARBONIC ANHYDRASE IX COMPLEX AND CONTRAST AGENT THEREOF

CROSS REFERENCE TO RELATED APPLICATION

This application claims the benefits of Taiwan application Serial No. 108142431, filed Nov. 22, 2019, the disclosures of which are incorporated by references herein in its entirety.

BACKGROUND

Technical Field

The present disclosure relates to the field of radiological imaging and diagnosis, and in particular to a complex with two different types of IX molecules bonded to carbonic anhydrase.

Related Art

Tumor hypoxia is a characteristic of the tumor microenvironment, and the oxygen content of most of tumor tissue is 3% or below. In such an environment, tumor cell apoptosis is inhibited by signal transduction pathways, and the activity of drug efflux channels in the cell membrane or tumor cells enter a dormant state, affecting the radiotherapy and chemotherapy. Clinically the polarographic oxygen electrode is used as a gold standard inspection method, which is carried out by piercing a tumor part with a metal probe, and is an invasive inspection. Though the method is precise, results of repeated tests may vary with different piercing positions, and the inspection cannot be carried out on deep tissue (brain, liver, kidney and large intestine). In addition, near infrared spectroscopy can also be adopted clinically, which, however, has limited effects compared with augmented computed tomography, Doppler ultrasound and the like.

In the field of contrast agents for tumor hypoxia, $^{18}$F-MISO is clinically the most widely applied at present. However, studies show that this drug has low cellular absorptivity, making it difficult to enter cells smoothly to act on hypoxia-associated enzymes. As a result, the tumor hypoxia part cannot be accurately determined by PET/CT imaging. Furthermore, $^{18}$F-MISO lacks specificity and can be absorbed by both normal and hypoxia cells. Once the drug enters normal tissue, it cannot be eliminated or expelled in time due to the low drug clearance rate, leading to the generation of drug signals in the normal tissue which affect the judgment. Moreover, because F-18 is a nuclide having a short half-life, the inspection time is limited. In addition, $^{18}$F-MISO exhibits a high uptake variability, resulting in poor reproducibility. In view of this, an improved peptide drug is urgently needed in the art to overcome the defects of the related art.

SUMMARY

To enable the reader to understand the basic idea of the present disclosure, the summary section provides a brief description of the present disclosure. The summary section is not a complete description of the present disclosure, and is not intended to define the technical features or the scope of the present disclosure.

An aspect of the present disclosure relates to a dual-targeted carbonic anhydrase IX complex which includes: a binding peptide or a fragment or derivative thereof, where the binding peptide has an amino acid sequence of SEQ ID NO: 1 (NHVPLSP); a sulfonamide derivative coupled with the binding peptide; and a metal chelating agent coupled with the binding peptide and the sulfonamide derivative.

According to an embodiment of the present disclosure, in the dual-targeted carbonic anhydrase IX complex, the binding peptide is connected with the sulfonamide derivative through a linker. Specifically, the linker includes a plurality of glycines and one cysteine. In a specific embodiment, the linker includes six glycines.

In an optional embodiment, the metal chelating agent is selected from a group consisting of 1,4,7,10-tetraazacyclododecane-1,4,7,10-tetraacetic acid (DOTA), 1,4,7-triazacyclononane-1,4,7-triacetic acid (NOTA), 1,4,7-triazacyclononane-1,4-diacetic acid (NODA) and diethylenetriaminepenta-acetic acid (DTPA).

According to another embodiment of the present disclosure, the dual-targeted carbonic anhydrase IX complex further includes a radioactive substance marking the metal chelating agent, where the radioactive substance is selected from a group consisting of Ga-66, Ga-67, Ga-68, Zr-89, Lu-177, In-111 and I-123.

According to an embodiment of the present disclosure, the sulfonamide derivative of the dual-targeted carbonic anhydrase IX complex is acetazolamide.

Another aspect of the present disclosure relates to a contrast agent which includes the dual-targeted carbonic anhydrase IX complex of any above embodiment, and a contrast excipient.

Those of ordinary skill in the art can fully learn the central concept of the present disclosure, the technical means adopted and various implementation aspects from the following detailed description of embodiments.

BRIEF DESCRIPTION OF THE DRAWINGS

To make the foregoing and other objectives, features, advantages, and embodiments of the present disclosure more obvious and comprehensible, the accompanying drawings are described as follows.

DETAILED DESCRIPTION

To make the descriptions of the present disclosure more thorough and complete, implementation aspects and specific embodiments of the present disclosure are described below in an illustrative manner. However, the implementation aspects and specific embodiments of the present disclosure are not limited thereto.

Unless otherwise defined, meanings of all scientific and technical terms used in the present disclosure are the same as that usually understood and used by those skilled in the art. In addition, terms used in this specification all cover the singular form and the plural form of the terms, unless otherwise specified.

As described in this specification, "about" usually refers to that an actual value is within ±10%, ±5%, ±1%, or ±0.5% of a specific value or range. The term "about" in this specification represents that the actual value falls within an acceptable standard error of an average value, and is determined according to consideration by those of ordinary skill in the art. In addition to experiment or unless otherwise explicitly specified, it may be understood that the range, the quantity, the value, and the percentage used herein are all modified by "about". Therefore, unless otherwise stated, values or parameters disclosed in this specification and the scope of appended claim are approximate values, and may be changed as required.

In order to solve the problems in the related art, an objective of the present disclosure is to provide a novel dual-targeted carbonic anhydrase IX complex for tumor hypoxia diagnosis. The dual-targeted carbonic anhydrase IX complex has the advantages of non-invasive property, low cost, synthesis convenience, good reproducibility, high gathering degree at tumor hypoxia parts and low in-vivo background value and has potential for use as a molecular nuclear diagnosis drug. Based on these advantages, the complex provided by the present disclosure can overcome the defects of the $^{18}$F-MISO and can also be used to replace the polarographic oxygen electrode approved for clinical use to clinically improve the accuracy in determining the tumor hypoxia degree.

Figure 1:
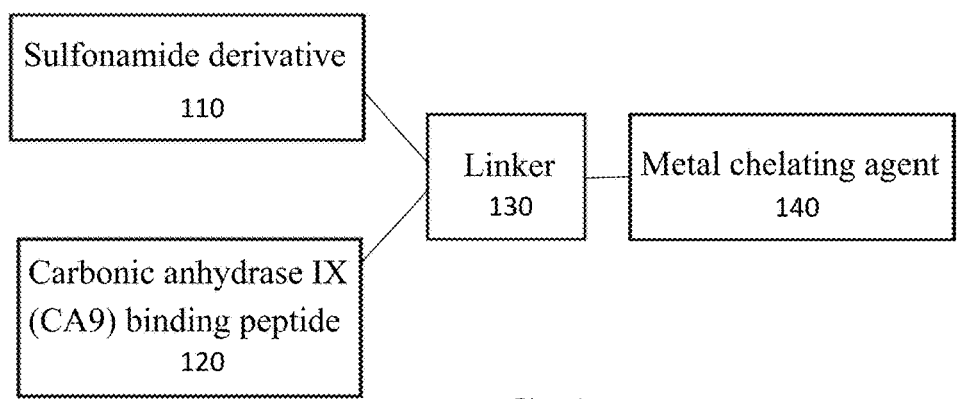
FIG. 1 is a schematic structural diagram of a dual-targeted carbonic anhydrase IX complex according to an embodiment of the present disclosure.

The structure of the dual-targeted carbonic anhydrase IX complex of the present disclosure is as shown in FIG. 1. The complex mainly includes a sulfonamide derivative 110, a carbonic anhydrase IX (CA9) binding peptide 120, a linker 130 and a metal chelating agent 140. In an optional embodiment, the sulfonamide derivative 110 may be sulfanilamide, 4-cyanobenzene-1-sulfonamide, 5-(aminomethyl)thiophene-2-sulfonamide, 4-(2-aminoethyl)benzenesulfonamide, 6-aminopyridine-3-sulfonamide, 5-(2-aminoethyl)thiophene-2-sulfonamide and 2-amino-N,N-dimethyl-1,3-benzothiazole-6-sulfonamide, preferably acetazolamide (AAZ). The CA9 binding peptide 120 has an amino acid sequence of SEQ ID NO: 1. The linker 130 may consist of a plurality of amino acids and has amino acid sequences of, for example, GGGCGGG (SEQ ID NO: 2), GGGGCGGGG (SEQ ID NO: 3), GGGGGCGGGGG (SEQ ID NO: 4) and GGGGGGCGGGGGG (SEQ ID NO: 5).

In other embodiments, the linker 130 has an amino acid peptide sequence of GnCGn, where n is at least 3-6 or more.

The metal chelating agent 140 is selected from a group consisting of 1,4,7,10-tetraazacyclododecane-1,4,7,10-tetraacetic acid (DOTA), 1,4,7-triazacyclononane-1,4,7-triacetic acid (NOTA), 1,4,7-triazacyclononane-1,4-diacetic acid (NODA) and diethylenetriaminepenta-acetic acid (DTPA). In a specific embodiment, the metal chelating agent is DOTA. In addition, nuclide suitable for marking the complex of the present disclosure includes, but is not limited to, Ga-66, Ga-67, Ga-68, Zr-89, Lu-177, In-111 and I-123. In an embodiment, the radioactive substance is In-111.

Moreover, another aspect of the present disclosure is a preparation method of the dual-targeted carbonic anhydrase IX complex. Step 1. The carbonic anhydrase IX (CA9) binding peptide and the sulfonamide derivative (AAZ) are directly synthesized through a peptide synthesizer, where the linker between dual-targeted probes mainly includes six glycines and one cysteine and has an amino acid sequence of SEQ ID NO: 2. Step 2. The cysteine of the product of the previous step is bonded with maleimide-DOTA. Step 3. Finally the product in step 2 is marked with the radioactive substance to obtain the dual-targeted carbonic anhydrase IX (CA9) complex of the present disclosure.

The following discloses a plurality of embodiments to describe various different implementation aspects of the present disclosure, so that those skilled in the art can implement the technical contents of the present disclosure according to the descriptions in this specification. Therefore, the embodiments disclosed below are not intended to limit the scope of the present disclosure. In addition, all documents cited in this specification shall be construed as being incorporated in this specification by reference.

Example 1 Synthesis of $^{111}$In-DOTA-AAZ-CA9tp

Example 1.1 Preparation of AAZ-CA9tp a) 10 g of AAZ was added to 37% concentrated hydrochloric acid to react at room temperature for 2 h in a reflux unit, and then subjected to acid and alkali neutralization (pH=7) with NaOH to obtain 5-amino-1,3,4-thiadiazole-2-sulfonamide.

b) Then, 5-amino-1,3,4-thiadiazole-2-sulfonamide, 0.1 M succinic anhydride and 100 mL of dimethylformamide (DMF) reacted at 100° C. for 4 h to obtain AAZ (AAZ-COOH) with a carboxylic acid group.

c) Bonding synthesis of the peptide and AAZ-COOH was carried out by a microwave heating solid-phase peptide synthesis system (brand: CEM, model: liberty Blue).

d) A peptide synthesis sequence (NHVPLSPGGGCGGG-AAZ) (SEQ ID NO: 6) was set first according to an operation mode of the instrument.

e) Solid-phase reaction resin was soaked and activated in the DMF at room temperature for 30 min and then put into a reaction tank.

f) Preparation quantities of required reaction solvents (DMF, piperidine and diisopropylcarbodiimide), amino acids and AAZ-COOH were displayed on a computer according to a type and weight of the resin.

g) A bonding procedure of each amino acid included cycles of deprotection, condensation and cleaning for an implementation time of about 15 min, and it took about 3.5-4 h to synthesize a whole peptide sequence.

h) The resin was taken out of the reaction tank and was put into a 50 mL centrifuge tube, and 10 mL of a reaction solution containing trifluoroacetic acid, secondary water, triisopropylsilane and dithiothreitol (a weight ratio of 88:5:5:2) was added to react at room temperature for 3 h for acid hydrolysis to cut off peptide fragments bonded to the resin.

i) 40 mL of diethyl ether was added to the centrifuge tube for centrifuging for 3-5 min at 4,000 rpm.

j) Supernate was removed, and precipitates were freeze-dried to obtain a synthesized peptide fragment (NHVPL-SPGGGCGGG-AAZ) (AAZ-CA9tp) (SEQ ID NO: 6).

k) Correctness of a molecular weight (1471.93 m/z) of the synthesized drug was confirmed by a mass spectrometer.

Example 1.2 Preparation of DOTA-AAZ-CA9tp (1) 50 mg of AAZ-CA9tp and 10 mg of maleimido-monoamide-DOTA were added to a 0.1 M phosphoric acid buffer solution (NaH$_2$PO$_4$ and Na$_2$HPO$_4$) with a pH of 6-6.5 to react at room temperature for 8 h, and the product was desalted and freeze-dried to obtain DOTA-AAZ-CA9tp.

(2) Correctness of a molecular weight (1990.43 m/z) of the bonded drug was confirmed by a mass spectrometer.

Example 1.3 Preparation of $^{111}$In-DOTA-AAZ-CA9tp (1) 10 mg of DOTA-AAZ-CA9tp and 5 mCi of Indium-111 (specific activity greater than 450 mCi/ml) were added to a 0.1 M (2-(N-morpholino)ethanesulfonic acid) buffer solution to react at 95° C. for 30 min to obtain a product $^{111}$In-DOTA-AAZ-CA9tp.

(2) A radiolabelling efficiency was analyzed by Instant Thin Layer Chromatography (iTLC). The mobile phase was 0.1 M ammonium acetate.

(3) The result showed that the radiolabelling efficiency was greater than 98%.

DOTA-AAZ-CA9tp reacted with In-111 at 95° C. for 30 min in a 0.1 M MES buffer solution. Then, a radiolabelling efficiency was analyzed by Instant Thin Layer Chromatography (iTLC), and a mobile phase was 0.1 M ammonium acetate. The result showed that free In-111 was located at an original point, and a radiolabelling efficiency of $^{111}$In-DOTA-AAZ-CA9tp was greater than 98%.

Example 2 Colorectal Cancer Animal Contract of $^{111}$In-DOTA-AAZ-CA9tp

Experimental Method and Process (1) Each BALB/c nude mouse that was 8 weeks old was subjected to subcutaneous injection of human colorectal cancer cells (HCT15, 1*10$^6$ cells) on a right hind leg, grew for 10-14 d, and started to be dosed with the drug when a cell tumor grew to a size of 50-100 mm$^3$.

(2) Each animal was dosed in a caudal vein mode at a dosage of 25 mCi/kg for four groups of animals (control groups: $^{111}$In-DOTA, $^{111}$In-DOTA-AAZ and $^{111}$In-DOTA-CA9 and experimental group: $^{111}$In-DOTA-AAZ-CA9tp).

(3) NanoSPECT/CT image analysis was carried out at $2^{nd}$ h, $4^{th}$ h, $24^{th}$ h and $48^{th}$ h after animal dosage (brand: Mediso).

(4) Obtained images were subjected to image recombination and outputting by VivoQuamt software.

Experimental Results (1) In the experimental group, there had already been drug signals at the tumor part (right hind leg) of the experimental group ($^{111}$In-DOTA-AAZ-CA9tp) at $2^{nd}$ h, which meant that the drug can arrive at a tumor hypoxia position within a short time and a drug gathering degree at $24^{th}$ h after dosage was the highest. The experimental results are as shown in FIG. 2.

Figure 2:
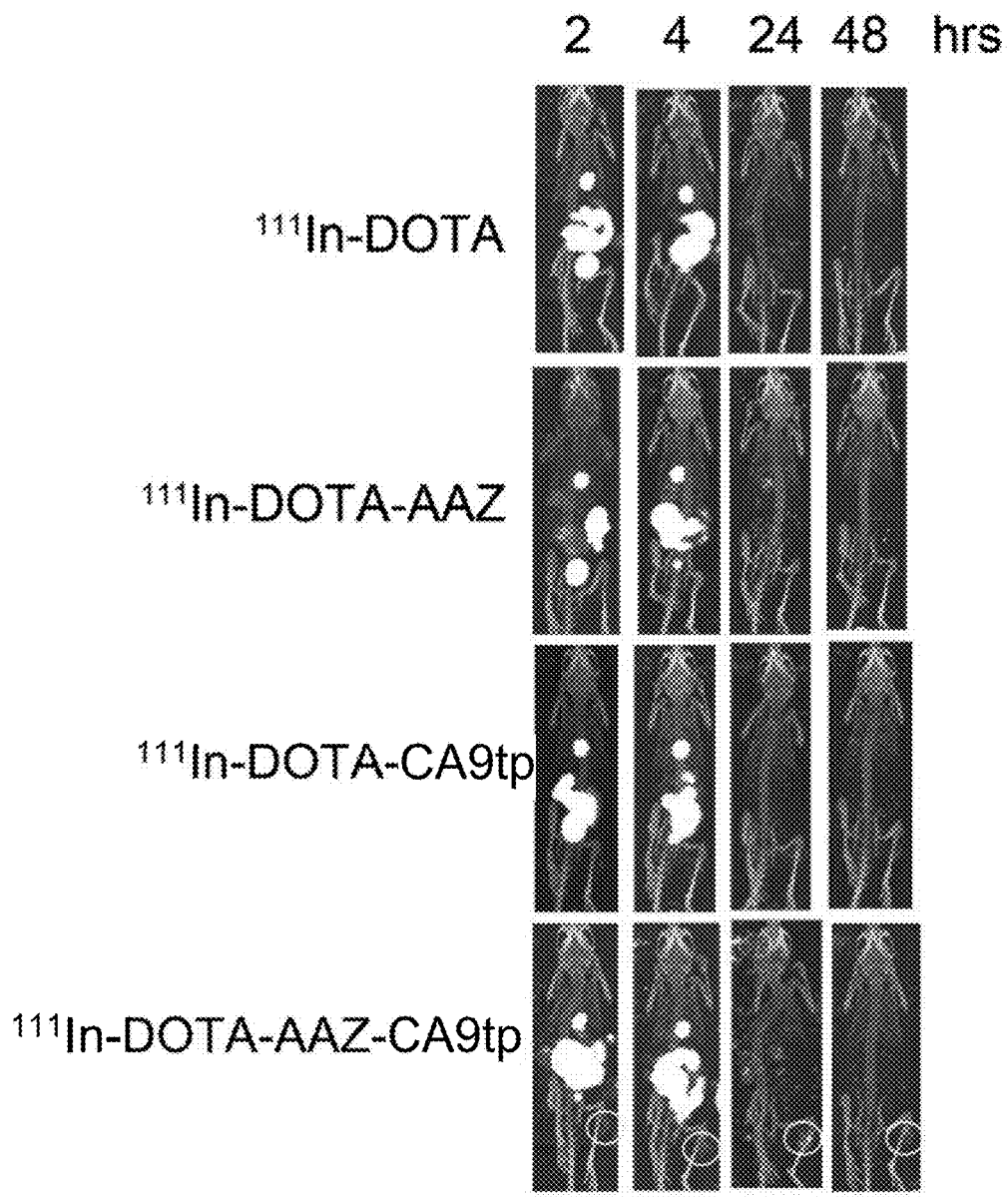
FIG. 2 shows nanoSPECT/CT images of a colorectal cancer animal model of the dual-targeted carbonic anhydrase IX complex according to an embodiment of the present disclosure.

(2) Compared with other groups ($^{111}$In-DOTA, $^{111}$In-DOTA-AAZ and $^{111}$In-DOTA-CA9) where no obvious drug gathering phenomenon happened at a tumor hypoxia position, the experimental group proved that the dual-targeted carbonic anhydrase IX complex had an excellent inspection ability, and the experimental results are as shown in FIG. 2.

Heterotransplantation animals induced by HCT15 cells started to be subjected to caudal vein drug dosage when a tumor grew to a size of about 50-100 mm$^3$. $^{111}$In-DOTA, $^{111}$In-DOTA-AAZ and $^{111}$In-DOTA-CA9 served as control groups, $^{111}$In-DOTA-AAZ-CA9tp served as an experimental group, and nano SPECT/CT contrast was carried out at $2^{nd}$ h, $4^{th}$ h, $24^{th}$ h and $48^{th}$ h after dosage.

Example 3 Colorectal Cancer Animal Bio-Distribution of $^{111}$In-DOTA-AAZ-CA9tp Experimental Method and Process (1) Each BALB/c nude mouse that was 8 weeks old was subjected to subcutaneous injection of human colorectal cancer cells (HCT15, 1*10$^6$ cells) on a right hind leg, grew for 10-14 d, and started to be dosed with the drug when a cell tumor grew to a size of 50-100 mm$^3$.

(2) Each animal was dosed in a caudal vein mode at a dosage of 25 mCi/kg for four groups of animals (control groups: $^{111}$In-DOTA, $^{111}$In-DOTA-AAZ and $^{111}$In-DOTA-CA9 and experimental group: $^{111}$In-DOTA-AAZ-CA9tp).

(3) There were four time points in each group and three mice at each time point.

(4) The animals were sacrificed at $2^{nd}$ h, $4^{th}$ h, $24^{th}$ h and $48^{th}$ h after dosage to take organs (brain, heart, lung, liver, kidney, spleen, stomach, large intestine, small intestine, tumor, muscle and blood).

(5) Tissue organs were weighed, and radioactivities were counted and read by a gamma counter.

(6) With a percentage (%) of a radioactivity count of Injected Dose (ID) in a radioactivity count of each gram (g) of tissue as unit (% ID/g), the line graph was drawn for showing.

Figure 3:
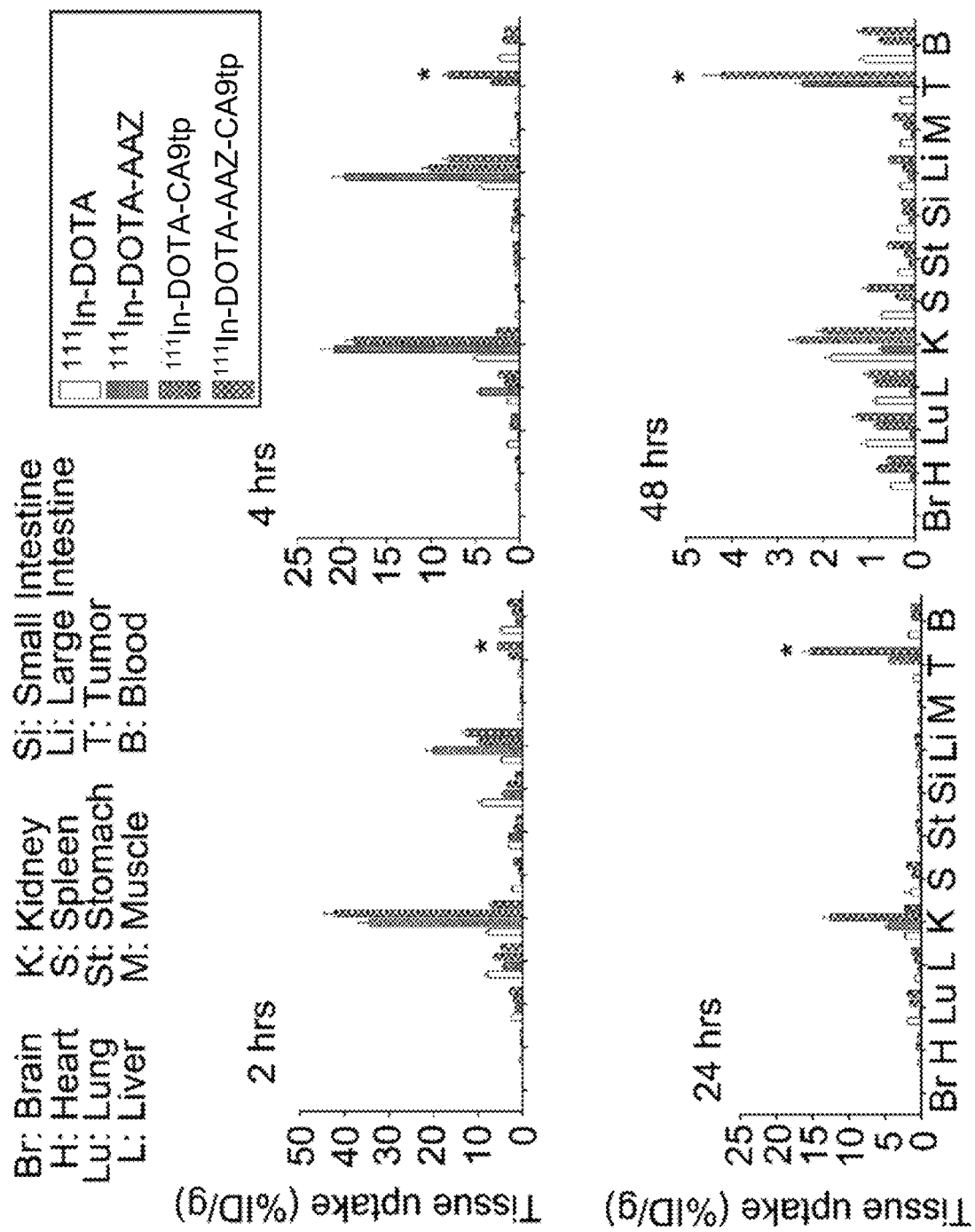
FIG. 3 is a line graph of tumor uptake results of a tumor animal model of the dual-targeted carbonic anhydrase IX complex according to an embodiment of the present disclosure.

Experimental Results (1) In the experimental group, there were drug signals at the tumor part of the experimental group ($^{111}$In-DOTA-AAZ-CA9tp) at $2^{nd}$ h, and tumor absorbability was about 5.42% ID/g, greater than that of control groups ($^{111}$In-DOTA: 0.88% ID/g, $^{111}$In-DOTA-AAZ: 0.35% ID/g, and $^{111}$In-DOTA-CA9: 2.99% ID/g), which meant that the drug can arrive at a tumor hypoxia position within a short time. The experimental results are as shown in FIG. 3.

(2) $^{111}$In-DOTA-AAZ-CA9tp had the highest gathering degree (about 15.38% ID/g) at the tumor hypoxia position at $24^{th}$ h, which was obviously higher than that of other groups ($^{111}$In-DOTA: 1.08% ID/g, $^{111}$In-DOTA-AAZ: 0.13% ID/g and $^{111}$In-DOTA-CA9: 4.32% ID/g), which proved that the dual-targeted carbonic anhydrase IX complex had an excellent inspection ability. The experimental results are as shown in FIG. 3.

Figure 4:
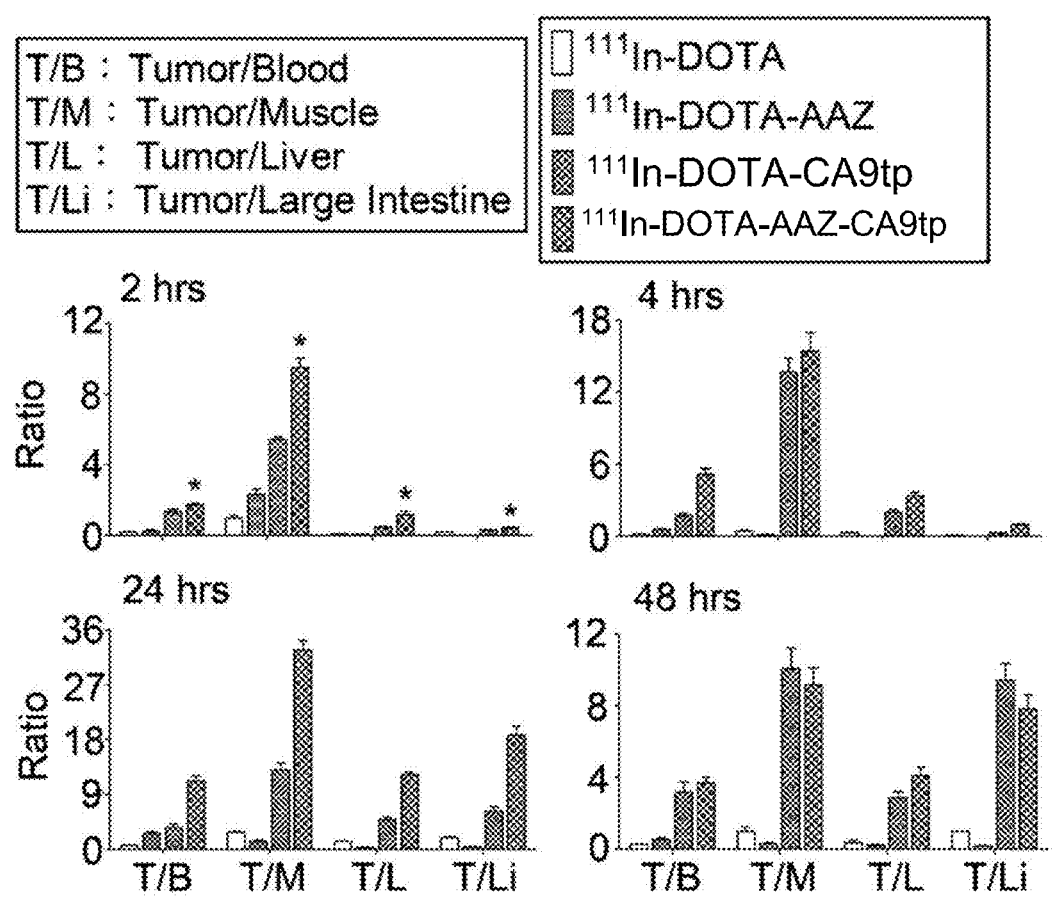
FIG. 4 shows ratios of tumor/muscle, tumor/blood, tumor/liver and tumor/large intestine in a tumor animal model of the dual-targeted carbonic anhydrase IX complex according to the embodiment of FIG. 3.

(3) By analyzing ratios of tumor absorption to blood, muscle, liver and large intestine in the four groups of drugs ($^{111}$In-DOTA, $^{111}$In-DOTA-AAZ, $^{111}$In-DOTA-CA9 and $^{111}$In-DOTA-AAZ-CA9tp) respectively, the ratios of the $^{111}$In-DOTA-AAZ-CA9tp group at $2^{nd}$ h to $24^{th}$ h were all better than those of other groups, and the experimental results are as shown in FIG. 4.

Heterotransplantation animals induced by HCT15 cells started to be subjected to caudal vein drug dosage when a tumor grew to a size of about 50-100 mm$^3$, $^{111}$In-DOTA, $^{111}$In-DOTA-AAZ and $^{111}$In-DOTA-CA9 served as control groups, $^{111}$In-DOTA-AAZ-CA9tp served as an experimental group, and mice were sacrificed at $2^{nd}$ h, $4^{th}$ h, $24^{th}$ h and $48^{th}$ h after dosage, brain, heart, lung, liver, kidney, spleen, stomach, small intestine, large intestine, muscle, tumor and blood were collected, and finally inspection was carried out by the gamma counter. The value was a percentage of Injected Dose in each gram of organs (% ID/g). Data was represented by an average value±SEM (n=3). *P<0.05 compared with the control group ($^{111}$In-DOTA-CA9), and the results were shown in FIG. 3. In addition, the ratios of tumor/muscle, tumor/blood, tumor/liver and tumor/large intestine in $^{111}$In-DOTA-AAZ-CA9tp are as shown in FIG. 4, and the experimental results showed that the ratios reached the optimal value at $24^{th}$ h. *P<0.05 compared with the control group ($^{111}$In-DOTA-CA9). Data was represented by an average value ±SEM (n=3).

The content of the following submission on ASCII text file is incorporated herein by reference in its entirety: a computer readable form (CRF) of the Sequence Listing (file name: "1080288USI1_sequence.txt", date recorded: Oct. 27, 2022, size: 2 KB.)

What is claimed is:

1. A dual-targeted carbonic anhydrase IX complex, comprising:
   a binding peptide with an amino acid sequence of SEQ ID NO: 1 (NHVPLSP);
   a sulfonamide derivative coupled with the binding peptide; and
   a metal chelating agent coupled with the binding peptide and the sulfonamide derivative;
   wherein the sulfonamide derivative is acetazolamide.

2. The dual-targeted carbonic anhydrase IX complex according to claim 1, wherein the binding peptide and the sulfonamide derivative are connected through a linker.

3. The dual-targeted carbonic anhydrase IX complex according to claim 2, wherein the linker comprises a plurality of glycines and one cysteine.

4. The dual-targeted carbonic anhydrase IX complex according to claim 3, wherein the linker is selected from a group consisting of amino acid sequences of SEQ ID NO: 2, SEQ ID NO: 3, SEQ ID NO: 4 and SEQ ID NO: 5.

5. The dual-targeted carbonic anhydrase IX complex according to claim 1, wherein the metal chelating agent is selected from a group consisting of 1,4,7,10-tetraazacyclododecane-1,4,7,10-tetraacetic acid (DOTA), 1,4,7-triazacyclononane-1,4,7-triacetic acid (NOTA), 1,4,7-triazacyclononane-1,4-diacetic acid (NODA) and diethylenetriaminepenta-acetic acid (DTPA).

6. The dual-targeted carbonic anhydrase IX complex according to claim 1, further comprising a radioactive substance marking the metal chelating agent, wherein the radioactive substance is selected from a group consisting of Ga-66, Ga-67, Ga-68, Zr-89, Lu-177, In-111 and I-123.

7. A contrast agent, comprising:
   the dual-targeted carbonic anhydrase IX complex according to claim 1; and
   a contrast excipient.

* * * * *